United States Patent [19]

Amselem

[11] 3,957,981

[45] May 18, 1976

[54] PHARMACEUTICAL COMPOSITION COMPRISING VINCAMINE AND ACETYLSALICYCLIC ACID

[75] Inventor: Armand Amselem, Toulouse, France

[73] Assignee: Parcor, Paris, France

[22] Filed: Dec. 23, 1974

[21] Appl. No.: 536,941

[30] Foreign Application Priority Data
Dec. 28, 1973 France .............................. 73.46739

[52] U.S. Cl. ................................. 424/232; 424/262
[51] Int. Cl.² .............. A61K 31/475; A61K 31/625
[58] Field of Search ............................ 424/232, 262

[56] References Cited
OTHER PUBLICATIONS

U.S. Dispensatory — 25th edition, (1955), pp. 17 & 18.
Kisfaludy et al. — Chem. Abst. Vol. 73, (1970), p. 35598k.
Forschag — Chem. Abst. Vol. 78, (1973), p. 62167d.

*Primary Examiner*—Sam Rosen
*Attorney, Agent, or Firm*—Cushman, Darby & Cushman

[57] ABSTRACT

The herein disclosed invention is directed to pharmaceutical compositions of vincamine and acetylsalicylic acid having cerebral vasodilator activity.

10 Claims, No Drawings

PHARMACEUTICAL COMPOSITION COMPRISING VINCAMINE AND ACETYLSALICYCLIC ACID

The present invention relates to pharmaceutical compositions and in particular to a vaso-regulator composition for the cerebral blood circulation.

Thus the invention provides a pharmaceutical composition comprising vincamine or a non-toxic salt thereof and acetylsalicylic acid or a non-toxic salt thereof.

Vincamine, discovered by E. S. Zabolotnaja in 1950, is the main alkaloid of the small periwinkle; vinca minor (Apocynaceae).

It has the empirical formula $C_{21}H_{26}O_3N_2$ and the following structural formula:

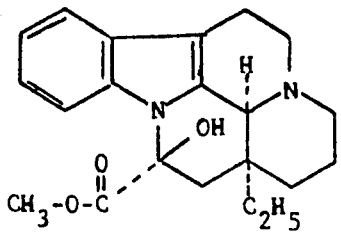

Its synthesis is described by Kuehne in J. Am. Chem. Soc. 86, 2946 (1964).

Numerous publications have noted the many interesting physiological properties of this alkaloid, which is a cerebral vasodilator and oxygenator with a slight hypotensive and sedative effect.

The composition of the invention may contain, in place of basic vincamine, its non-toxic addition salts with mineral or organic acids and/or its quaternary ammonium derivatives.

Acetylsalicylic acid (or aspirin) and its non-toxic salts have long been known for their analgesic, anti-inflammatory and anti-pyretic properties. Some years ago, it was found that acetylsalicylic acid plays an important role in the mechanisms of haemostasis and in the pathogenesis of thromboses.

In these mechanisms, blood platelets play an important role and the study of them has shown that the agglomeration of platelets is the result of a sequence of reactions. Numerous substances are capable of intervening to interrupt this succession of processes. These substances, which inhibit the agglomeration of platelets, thus possess an anti-thrombotic activity which is very valuable to patients suffering from thrombo-embolic diseases.

Used alone, in all manifestations of cerebral circulatory deficiency, vincamine considerably increases the cerebral blood flow and permits better use of the oxygen in the blood in these areas.

Acetylsalicylic acid, by inhibiting the agglomeration of platelets and thus the formation of groups of platelets, which are at the root of embolisms, has a favourable effect in the restoring of ischemic cerebral tissue.

Our experiments have shown that in the presence of acetylsalicylic acid the action of vincamine on the cerebral blood flow is increased and that the combination of vincamine or one of its derivatives and acetylsalicylic acid had a clearly greater haemodynamic action both qualitatively and quantitatively.

This activity was demonstrated in the pharmacological study reported hereinafter together with the toxicological study.

I. TOXICOLOGICAL STUDY

This study related to:
a. the acute toxicity of vincamine, acetylsalicylic acid and the combination according to the invention,
b. the chronic toxicity,
c. the delayed toxicity, and
d. local and general tolerance and allowed us to confirm that the composition of the invention is tolerated perfectly in the conditions of the experiment, whether administered by the oral, parenteral or rectal routes, without provoking any local or general reaction whatsoever.

The toxicity of the compositions of the invention is the same as that of its constituents and, from this point of view, no potentiation at all was established.

II. PHARMACOLOGICAL STUDY

This study related to the inhibiting action on the agglomeration of platelets and to the vasodilatory action.

A. Inhibiting Action on the Agglomeration of Platelets

Rat serum, rich in platelets and normally cloudy, is clarified by the addition of adenosine diphosphate, which causes agglomeration of the platelets. If the same test is carried out with serum taken from an animal which has been given the composition of the invention, containing 30 mg/kg of vincamine and 175 mg/kg of acetylsalicylic acid, agglomeration of the platelets does not occur and the serum remains cloudy. Measurement of the optical density with a spectrophotometer thus permits the evaluation the inhibiting power of the composition tested on the agglomeration of platelets.

It is thus shown that the administration of a composition of the invention protects the experimental animals from the agglomeration of platelets to a large and significant degree.

B. Vaso-dilatory Action

The experiments were carried out on dogs. The administration per os, of the combination according to the invention, containing 30 mg/kg of vincamine and 175 mg/kg of acetylsalicylic acid, then of 30 mg of vincamine alone, demonstrated the clearly increased effect produced by the composition of the invention; the rheographic study showed that the blood flow in the vertebral artery, which is the chief supply route to the brain, is on average increased by 35 percent in animals which have been given vincamine alone, and by 51 percent in dogs to which both vincamine and acetylsalicylic acid, i.e. the combination of the invention, have been administered. This increase in blood flow in the vertebral artery is accompanied by an increase in blood pressure in the internal maxillary vein of 41 percent in the former case (vincamine only) and 66 percent in the latter case (vincamine and acetylsalicylic acid).

The pharmacological study reported above clearly shows the importance of the combinatiion of vincamine and acetylsalicylic acid according to the invention. The vasodilatory effect of vincamine on the cerebral circulation is increased to a remarkable extent in the presence of acetylsalicyic acid which, by its inhibiting effect on the agglomeration of platelets, permits better blood circulation, particularly with respect to cerebral circulation.

Owing to this remarkable effect on the agglomeration of platelets and cerebral blood flow, the composition according to the invention may be advantageously used in human and veterinary medicine.

The active principles are generally formulated with a therapeutically acceptable carrier. Thus, the composition may advantageously be formulated as tablets, coated tablets and capsules for oral administration.

It may also be presented for rectal administration in the form of suppositories, and for administration by the parenteral route.

In general, the ratio by weight of vincamine to aspirin is from 0.01 to 0.1 and preferably from 0.025 to 0.075. The composition may be presented in dosage unit form, each individual dose advantageously containing from 0.005 to 0.050 g of vincamine and from 0.050 to 0.500 g of acetylsalicylic acid. The daily dose may vary from 0.005 to 0.150 g for vincamine and from 0.050 to 1.5 g for acetylsalicylic acid.

The following examples illustrate compositions in accordance with the invention.

Example 1
TABLETS

| | | |
|---|---|---|
| | vincamine | 0.020 g |
| | acetylsalicylic acid | 0.500 g |
| | rice starch | 0.005 g |
| | lactose | 0.010 g |
| | magnesium stearate | 0.005 g |
| | talc | 0.003 g |
| | yellow-orange S | Traces |

Example 2
COATED TABLETS

| | | |
|---|---|---|
| | vincamine | 0.015 g |
| | acetylsalicylic acid | 0.300 g |
| | magnesium stearate | 0.010 g |
| core | maize starch | 0.005 g |
| | calcium phosphate | 0.010 g |
| | shellac | 0.002 g |
| | gelatin | 0.010 g |
| | gum arabic | 0.005 g |
| coating | crystallised sugar | 0.010 g |
| | calcium sulphate | 0.005 g |
| | talc | 0.002 g |
| | titanium oxide | 0.002 g |
| | carnauba wax | 0.001 g |
| | white beeswax | 0.002 g |
| | sugar q.s.p. | 1 coated tablet |

Example 3
CAPSULES

| | |
|---|---|
| vincamine | 0.010 g |
| acetylsalicylic acid | 0.200 g |
| talc | 0.020 g |
| magnesium stearate | 0.010 g |

Example 4
SUPPOSITORIES

| | |
|---|---|
| vincamine | 0.015 g |
| acetylsalicylic acid | 0.200 g |
| semi synthetic triglycerides q.s.p. | 1 suppository |

It will be appreciated that our tests indicate that on account of its cerebral vasodilatory properties and its inhibiting effect on the agglomeration of platelets, the compositions of the invention increase blood flow and reduce the risk of accidents in patients suffering from thrombo-embolic diseases.

What we claim is:

1. A pharmaceutical composition comprising 0.005 to 0.050 grams vincamine and 0.50 to 0.500 grams acetylsalicylic acid, the weight ratio of vincamine to said acid being 0.01 to 0.1:1.

2. Composition as claimed in claim 1, which comprises vincamine as a non-toxic salt thereof.

3. Composition as claimed in claim 1, which comprises said acid as a non toxic salt thereof.

4. Composition as claimed in claim 1 in the form of tablets.

5. Composition as claimed in claim 1 in the form of capsules.

6. Composition as claimed in claim 1 in the form of a suppository.

7. A process for treating a patient suffering of a thrombo-embolic disease comprising administering to said patient from 0.005 to 0.150 g vincamine ad from 0.050 to 1.5 g of acetylsalicylic acid per 24 hours.

8. Process as claimed in claim 7, wherein vincamine is administered as a non toxic salt thereof.

9. Process as claimed in claim 7, wherein acetylsalicylic acid is administered as a salt thereof.

10. Process as claimed in claim 7, wherein vincamine and acetylsalicylic acid are administered as dosage units, each comprising 0.005 to 0.050 g vincamine and 0.050 to 0.500 g acetylsalicylic acid.

* * * * *